United States Patent [19]

Floyd et al.

[11] 4,334,546

[45] Jun. 15, 1982

[54] COSMETIC PENCIL

[75] Inventors: David T. Floyd, Milford; John H. Murphy, Matamoras; John J. Brodzinski, Milford, all of Pa.

[73] Assignee: Kolmar Laboratories Inc., Port Jervis, N.Y.

[21] Appl. No.: 185,229

[22] Filed: Sep. 8, 1980

[51] Int. Cl.³ .......................................... A45D 40/30
[52] U.S. Cl. .................................................. 132/88.5
[58] Field of Search ...................... 132/73, 73.5, 74.6, 132/88.5, 88.7

[56] References Cited

U.S. PATENT DOCUMENTS 1,819,004  8/1931  Roessinger ............................ 132/73
2,449,070  9/1948  Hauser ............................ 132/73 UX

FOREIGN PATENT DOCUMENTS 50-78474   7/1975  Japan .
52-32471   3/1977  Japan .
53-46850   4/1978  Japan .
53-61281   5/1978  Japan .
53-161078 12/1978  Japan .
54-8937    4/1979  Japan .
54-18382   7/1979  Japan .

*Primary Examiner*—G. E. McNeill
*Attorney, Agent, or Firm*—Andrus, Sceales, Starke & Sawall

[57] ABSTRACT

A cosmetic pencil for use in the topical application of eye shadow, eye liner, lipstick, or the like. The pencil comprises an outer sheath or barrel and an inner core of a cosmetic composition. The barrel is composed of polyethylene and contains from 5% to 20% by weight of hydrogenated castor oil. The cosmetic pencil can be readily sharpened through use of a conventional pencil sharpened, and the addition of the hydrogenated castor oil provides the barrel with increased toughness, easier sharpening characteristics, as well as substantially reducing stress cracking of the barrel at elevated temperatures.

11 Claims, No Drawings

COSMETIC PENCIL

BACKGROUND OF THE INVENTION

Cosmetic pencils are commonly used for the application of eye shadow, eye liner, or lipstick, and are composed of an outer barrel or sheath and an inner core of a wax-like cosmetic material. Traditionally, the barrel has been formed of wood by gluing together two longitudinally split halves, and because of this method of manufacture, hot melted cosmetic core material could not be poured directly into the barrel or the heat would destroy the glued joint in the wood barrel. Consequently, the traditional practice has been to insert the pre-formed rods of the core material into the tubular wood barrel which is a difficult processing operation. As a result, only harder type core materials are usable with a wood barrel.

As a further problem, the wood barrels are produced from tight grain cedar which is only available in certain parts of the world, and recently, the quantities of this type of cedar have been extremely limited.

When using cosmetic materials that incorporate a volatile solvent, the solvent can "wick through" or penetrate the wood barrel. To prevent the loss of solvent, it has been necessary in the past to line the barrel with an impervious material, such as metal foil, and this further increases the cost of manufacture.

Some wood barrels, depending on the characteristics of the wood, are difficult to sharpen with a conventional sharpener and tend to break away in small fragments which can embed in the cosmetic core, resulting in a scratchy application to the skin.

Wood barrels are also sensitive to heat and humidity conditions, and may warp or split under high humidity.

As the wood barrels are normally made of cedar, the cedar odor tends to distort any fragrances incorporated in the cosmetic core material.

More recently, cosmetic pencils have been introduced into the market utilizing a polyethylene-type sheath or barrel. The polyethylene barrel has distinct advantages over the wood barrel in that it is more resistant to heat and humidity conditions and can be more easily processed or manufactured.

Though the polyethylene-type barrel can be sharpened with a conventional pencil sharpener, it has been observed that the shavings have a brittleness that results in plastic particles embedding themselves in the core product which affects the application. In contrast to the wood barrel, the polyethylene-type barrel is odorless, so that it is possible to use fragranced products whose odor will not be distorted.

However, it has been observed that the polyethylene-type barrel is subjected to stress cracking at temperatures in the range of 40° C. to 50° C., with the result that volatile solvents, that may be contained within the cosmetic core, can escape to the atmosphere, resulting in a drying out of the cosmetic composition. In addition, the commonly polyethylene-type barrel is pervious to some materials, so that they cannot be successfully incorporated in the barrel.

As a further disadvantage, the conventional polyethylene-type barrel is not compatible with many colorants, particularly pearlescents, with the result that the polyethylene-type barrel is limited by the colors that can be utilized.

SUMMARY OF THE INVENTION

The invention is directed to an improved cosmetic pencil, and more particularly, to an improved polyethylene barrel which has increased toughness to provide more uniform and less brittle sharpening characteristics. The barrel is also more resistant to stress cracking at elevated temperatures. The polyethylene barrel contains from 5% to 20%, and preferably about 9% to 10%, of hydrogenated or partially hydrogenated castor oil. The degree of hydrogenation is sufficient to provide the castor oil with a solidification temperature in excess of 50° C.

The addition of wax-like materials to polyethylene would normally be expected to soften the polyethylene, but in the present instance, the addition of the hydrogenated castor oil increases the toughness of the polyethylene, provided a more uniform cut or curl on sharpening, regardless of the pressure which is applied to the pencil.

The addition of the hydrogenated castor oil also provides a substantial improvement in the heat and humidity stability and reduces the tendency for the barrel to stress crack at elevated temperatures, so that volatile constituents in the cosmetic core and fragrances will not permeate through the barrel.

The cosmetic pencil of the invention is particularly adaptable to high speed manufacture. In processing, the molten cosmetic core material can be poured directly into the barrel, and as a result, both relatively hard and soft cosmetic compositions can be employed in the pencil.

As a further advantage, the polyethylene barrel composition of the invention is compatible with a wide range of coloring materials, including pearlescents.

DESCRIPTION OF THE PREFERRED EMBODIMENT

The invention is directed to a cosmetic pencil which comprises an outer sheath or barrel having a central bore which contains a cosmetic, pharmaceutical, or other type composition. The cosmetic pencil can be used for the application of eye shadow, eye liner, lipstick, fragrance stick, and similar types of products. In general, the outer diameter of the barrel may be in the neighborhood of ½ inch with a length of 4 inches. The diameter of the bore will generally be in the range of about ¼ inch.

In accordance with the invention, the barrel is composed of polyethylene and contains from 5% to 20% by weight of fully hydrogenated or partially hydrogenated castor oil, with about 9% to 10% of the castor oil being preferred. The degree of hydrogenation of the castor oil is sufficient to provide a solidification temperature in excess of 50° C. Castor oil is a natural oil and is generally considered to be a mixture of polyglycerides of the higher fatty acids, such as ricinoleic, oleic, linoleic, palmitic and stearic.

The polyethylene is a conventional type and in general has a softening point in the range of about 109° C. to 110° C. (ASTM E-28), a hardness (DMN) in the range of about 2.0 to 3.0 (ASTM D-5), and preferably about 2.5, and a viscosity in the range of 500 to 10,000 cps at 140° C. (Brookfield), and preferably about 4000 to 6000 cps.

The barrel can also contain up to 5% by weight, and preferably about 2.5%, of coloring materials, such as pigments and pearlescents. Examples of coloring materials that can be used are titanium dioxide, iron oxide, mica, bismuth oxychloride, calcium stearate, chrome oxide green, manganese violet, ultramarine pink, ferric ferrocyanide, ultramarine blue, iron blue oxide, and other coloring materials generally known in the cosmetic industry.

The polyethylene and hydrogenated castor oil can be admixed in various manners to provide the desired barrel composition. For example, beads or pellets of polyethylene and hydrogenated castor oil can be separately melted and then mixed together, or alternately, the castor oil can be melted and sprayed on polyethylene beads, or a dry blend of polyethylene beads and hydrogenated castor oil strands can be mixed and the resulting mixture then heated to a molten state.

The molten mixture is then poured by gravity, or injected or extruded into molds to form the barrel of the desired size and shape. After cooling and solidifying, the barrel has a Durometer hardness in the range of 45 to 55 on the D scale. This hardness is somewhat softer than polyethylene alone, but the barrel is considerably tougher due to the addition of the hydrogenated castor oil.

In the past, hydrogenated castor oil has been utilized with polyethylene, in small quantities up to about 1% by weight, as a mold release. It has been thought that greater quantities of wax-like hydrogenated castor oil would result in the polyethylene becoming friable or having a rubber-like consistency. However, contrary to the normal practice, it has been found that the addition of the substantial quantities of hydrogenated castor oil produces only a slight decrease in hardness, yet provides a substantial improvement in toughness, which results in a more uniform and continuous curl or shaving when the pencil is sharpened by a conventional pencil sharpener.

In addition to the substantial improvement in toughness, the addition of the hydrogenated castor oil improves the heat and humidity stability of the polyethylene barrel and reduces the tendency for stress cracking at elevated temperatures, thereby making it impervious to the passage of volatile constituents of the core, and certain fragrances.

As a further advantage, the barrel is more readily adaptable to coloring than normal polyethylene. There are certain colors, including pearlescents, which are not compatible with polyethylene making their use in polyethylene extremely limited. However, these colors, including pearlescents, can be initially incorporated with the hydrogenated castor oil and the mixture can then be added to the polyethylene. Thus, it is possible to use a much wider range of colors with the polyethylene-type barrel of the invention.

The following examples illustrate the manner of preparing the cosmetic pencil of the invention.

EXAMPLE I 9.77 parts by weight of Castorwax (N. L. Industries, Inc.), composed of hydrogenated castor oil having a solidification point of 86° C., was melted at a temperature ranging from 85° C. to 90° C. 1.50 parts by weight of Timica Sparkle (Mearl Corporation), 0.80 parts by weight of Timica Pale Gold (Mearl Corporation) and 0.03 parts by weight of Spectra Peal BKW (Mallinckrodt, Inc.) as colorants were added to the molten hydrogenated castor oil and mixed until uniform coloring was obtained. The molten mixture was then forced through a nozzle and cooled to form strands ⅛ inch in diameter. 43.95 parts by weight of polyethylene A-C 715 (Allied Chemical Co.) and 43.95 parts by weight of polyethylene A-C 735 (Allied Chemical Co.) were introduced into a Patterson-Kelley (P/K) blender and tumbled to mix. The wax colorant strands were than added to the blender and mixed with the polyethylene. By activating the intensifier bar in the P/K blender, the mixture was ground to a uniform particle size of ⅛ inch to ¼ inch.

The mixture was then charged into a hopper and injection molded by conventional equipment to provide on cooling, a cosmetic pencil barrel having an O/D. of ½ inch, and I/D of ¼ inch and a length of 4 inches.

The barrels as prepared above were subsequently filled by gravity pouring with a lipstick composition having the following formulation in parts by weight:

| | |
|---|---|
| Castor Oil | 17.55 |
| Lanolin | 7.45 |
| Petrolatum | 9.60 |
| Oleyl alcohol | 16.70 |
| Candelilla Wax | 15.50 |
| Ozokerite Wax | 4.00 |
| Beeswax | 4.00 |
| Carnauba Wax | 2.00 |
| Paraffin | 1.00 |
| Iron Oxides - 35% in Castor Oil | 20.70 |
| Titanium Dioxide - 55% in Castor Oil | 1.50 |

EXAMPLE II

Polyethylene barrels were prepared in the manner outlined in Example I and having the following composition in parts by weight:

| | |
|---|---|
| Polyethylene A-C ® 715 | 65.0 |
| Polyethylene A-C ® 735 | 27.4 |
| Castorwax MP-79 | 5.00 |
| Iron Oxides | 0.50 |
| Timica Sparkle | 2.10 |

The barrels were filled by gravity pouring with an eye shadow composition having the following formulation in weight percent:

| | |
|---|---|
| Stearic Acid | 4.50 |
| Candelilla Wax | 13.50 |
| Petrolatum | 20.35 |
| Beeswax | 2.00 |
| Octyl Dodecanol | 9.55 |
| Lanolin Acid | 11.50 |
| Peg-5 Soya Sterol | 4.60 |
| Mixed Pigments | 9.00 |
| Talc | 10.00 |
| Titanium Coated Mica | 15.00 |

EXAMPLE III

Polyethylene barrels were prepared in the manner outlined in Example I and having the following composition in parts by weight:

| | |
|---|---|
| Polyethylene A-C ® 715 | 24.30 |
| Polyethylene A-C ® 735 | 51.70 |
| Castorwax | 18.50 |
| Manganese Violet | 0.25 |

| -continued | |
|---|---|
| Timica Pale Gold | 4.25 |

EXAMPLE IV

Polyethylene barrels were prepared in the manner outlined in Example I and having the following composition in parts by weight:

| | |
|---|---|
| Polyethylene A-C® 715 | 10.00 |
| Polyethylene A-C® 735 | 79.65 |
| Castorwax | 10.00 |
| Mica | 0.10 |
| Chrome Oxide Green | 0.25 |

Various modes of carrying out the invention are contemplated as being within the scope of the following claims particularly pointing out and distinctly claiming the subject matter which is regarded as the invention.

We claim:

1. A cosmetic pencil, comprising an outer tubular barrel having an axial bore, and an inner core composed of a composition for topical application disposed within the bore, said barrel comprising from 5% to 20% by weight of hydrogenated castor oil with the degree of hydrogenation being such that the hydrogenated castor oil has a softening point above 50° C., and the balance being polyethylene, said barrel having improved toughness, improved sharpenability and increased resistance to stress cracking.

2. The pencil of claim 1, wherein said barrel has a Durometer hardness of 45 to 55 on the D scale.

3. The pencil of claim 1, wherein said polyethylene has a hardness in dmm (ASTM D-5) in the range of 2.0 to 3.0 and a viscosity in cps at 140° C. in the range of 500 to 10,000.

4. The pencil of claim 3, wherein said viscosity is in the range of 4000 to 6000.

5. The cosmetic pencil of claim 1, wherein said barrel also includes up to 5% of coloring materials.

6. A cosmetic pencil, comprising an outer tubular barrel having an axial bore, and an inner core composed of a composition for topical application disposed within the bore, said barrel comprising from 5% to 20% by weight of hydrogenated castor oil with the degree of hydrogenation being such that the hydrogenated castor oil has a softening point above 50° C., and the balance being polyethylene, said polyethylene having a hardness in dmm (ASTM D-5) in the range of 2.0 to 3.0 and a viscosity in cps at 140° C. in the range of 500 to 10,000.

7. The cosmetic pencil of claim 5, wherein said coloring material is a pearlescent material.

8. A method of forming a cosmetic pencil, comprising the steps of forming a molten composition comprising from 5% to 20% by weight of hydrogenated castor oil with the degree of hydrogenation being such that the hydrogenated castor oil has a softening point above 50° C. and the balance being polyethylene, pouring the molten mixture into a mold, solidifying the mixture to form a tubular barrel having a central bore, forming a molten topical composition suitable for topical application, pouring the molten topical composition into the central bore, and solidifying the topical composition to provide a cosmetic pencil.

9. The method of claim 8, and including the step of incorporating up to 5% by weight of colorants in said molten mixture.

10. A method of forming a cosmetic pencil, comprising the steps of incorporating cosmetic coloring materials with molten hydrogenated castor oil having a softening point above 50° C. to provide a colored blend, admixing the colored blend with polyethylene in an amount to provide a mixture containing from 5% to 20% by weight of hydrogenated castor oil, up to 5% by weight of said coloring material and the balance polyethylene, heating the mixture to provide a molten mixture, and molding the molten mixture to form a tubular colored barrel.

11. The method of claim 10, and including the step of utilizing pearlescents as the coloring material.

* * * * *